US006569177B1

(12) United States Patent
Dillard et al.

(10) Patent No.: US 6,569,177 B1
(45) Date of Patent: May 27, 2003

(54) ABLATION ATHERECTOMY BURR

(75) Inventors: David H. Dillard, Redmond, WA (US);
Garrett R. Beget, Bothell, WA (US);
Vittorino Monni, Seattle, WA (US)

(73) Assignee: SciMed Life Systems, Inc., Maple Grove, MN (US)

(*) Notice: Subject to any disclaimer, the term of this patent is extended or adjusted under 35 U.S.C. 154(b) by 168 days.

(21) Appl. No.: 09/769,191

(22) Filed: Jan. 19, 2001

(51) Int. Cl.[7] ............................................. A61B 17/32
(52) U.S. Cl. ..................................................... 606/168
(58) Field of Search ................................ 606/170, 171, 606/159, 180; 451/51, 61, 27, 541

(56) References Cited

U.S. PATENT DOCUMENTS

| 3,614,953 | A | | 10/1971 | Moss | |
|---|---|---|---|---|---|
| 4,002,169 | A | | 1/1977 | Cupler, II | |
| 4,196,547 | A | * | 4/1980 | Keske | 451/28 |
| 4,465,072 | A | | 8/1984 | Taberi | |
| 4,591,355 | A | | 5/1986 | Hilse | |
| 4,622,503 | A | | 11/1986 | Sundblom et al. | |
| 4,646,736 | A | | 3/1987 | Auth | |
| 4,669,465 | A | | 6/1987 | Moore et al. | |
| 4,990,134 | A | | 2/1991 | Auth | |
| 5,261,877 | A | | 11/1993 | Fine et al. | |
| 5,314,407 | A | | 5/1994 | Auth et al. | |
| 5,360,432 | A | | 11/1994 | Shturman | |
| 5,938,670 | A | | 8/1999 | Keith et al. | |
| 6,001,112 | A | | 12/1999 | Taylor | |
| 6,015,420 | A | * | 1/2000 | Wulfman et al. | 604/22 |
| 6,080,171 | A | | 6/2000 | Keith et al. | |
| 6,096,054 | A | | 8/2000 | Wyzgala et al. | |
| 6,146,395 | A | | 11/2000 | Kanz et al. | |
| 6,156,048 | A | | 12/2000 | Wulfman et al. | |
| 6,183,487 | B1 | | 2/2001 | Barry et al. | |
| 6,270,509 | B1 | | 8/2001 | Barry et al. | |
| 6,299,623 | B1 | | 10/2001 | Wulfman | |

FOREIGN PATENT DOCUMENTS

| EP | 0 229 620 B1 | 6/1992 |
|---|---|---|
| EP | 0 267 539 B1 | 4/1993 |
| WO | WO 96/10366 A1 | 4/1996 |

* cited by examiner

*Primary Examiner*—Rodney M. Lindsey
*Assistant Examiner*—James G Smith
(74) *Attorney, Agent, or Firm*—Christensen O'Connor Johnson Kindness PLLC

(57) ABSTRACT

An ablation burr for a rotational atherectomy device that may reduce the risk of damage to a vessel wall while providing ablative cutting surfaces out to the maximum diameter of the burr. Two different abrasive surfaces are provided on the leading surface of the ablation burr. A less aggressive or finer abrasiveness is provided near the ablation burr maximum diameter, which is the portion of the burr nearest the vessel wall. This portion of the burr also presents a relatively shallow angle of attach to the vessel wall. A more aggressive or coarser abrasive is applied to portions of the burr disposed further from the vessel wall. In one embodiment, the more aggressive abrasive portion of the burr has a concave profile, thereby further reducing the possibility that the more aggressive abrasive will contact the vessel wall, even when the burr is rotated significantly away from the vessel axis. The ablation burr body may be profiled with an offset or stepped sections on the leading surface that are dimensioned such that the abrasive particles do not extend radially beyond the maximum diameter of the smooth back surface of the ablation burr.

23 Claims, 5 Drawing Sheets

ABLATION ATHERECTOMY BURR

FIELD OF THE INVENTION

The present invention generally relates to medical devices and to ablative atherectomy burrs in particular.

BACKGROUND OF THE INVENTION

Vascular diseases, such as atherosclerosis and the like, have become quite prevalent in the modem day. These diseases may manifest themselves in a number of ways, often requiring different forms or methods of treatment for alleviating the adverse effects of the diseases. Vascular diseases, for example, may take the form of deposits or growths in a patient's vasculature which may restrict, in the case of a partial occlusion, or stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies have been developed. While effective invasive therapies are available, noninvasive therapies and minimally invasive therapies are desirable for many applications because these therapies generally decrease the chance of infection, reduce post-operative pain, and require less post-operative rehabilitation. Drug therapy is one type of noninvasive therapy developed for treating vascular diseases. Clot-busting drugs, for example, have been employed to help break up blood clots that may be blocking a particular vascular lumen.

Minimally invasive intravascular treatments exist that physically revascularize lumens. Two examples of such intravascular therapies are balloon angioplasty and atherectomy—both of which physically revascularize a portion of a patient's vasculature.

Balloon angioplasty is a procedure wherein a catheter is inserted into a patient's blood vessel through a relatively small puncture, which may be located proximate the groin. The catheter is intravascularly navigated by a treating physician to the occluded vascular site. The catheter includes an inflatable balloon or dilating member, which is placed adjacent the vascular occlusion and is then inflated. When the occluding deposit is relatively pliable, intravascular inflation of the dilating member, typically to a pressure on the order of 5 to 12 atmospheres or so, causes the balloon to displace the occluding matter towards the vessel walls and thereby restore substantially normal blood flow through the treated portion of the vasculature. It should be recognized that this procedure does not remove the matter from the patient's vasculature, but displaces and reforms it.

While balloon angioplasty is frequently successful in revascularizing vascular lumens by reforming the occluded material, some occlusions are not amenable to treatment with this procedure. For example, some intravascular occlusions are composed of an irregular, loose, or heavily calcified material which may extend relatively far along a vessel or may extend adjacent a side branching vessel, and thus may not be prone or susceptible to angioplastic treatment. Even if angioplasty is successful, there is a chance that the occlusion may recur. Recurrence of an occlusion may require repeated or alternative treatments given at the same intravascular site.

Another class of minimally invasive, revascularizing devices has been developed that physically removes at least a portion of the material occluding a vascular lumen. Such treatment devices, sometimes referred to as atherectomy devices, use a material removal instrument, such as a rotating cutter or ablater, for example, to remove the occluding material. The material removal instrument is typically attached to the distal end of a flexible drive shaft that extends from an electric motor or compressed-gas-driven turbine through the patient's vasculature to the site of the occlusion.

In operation, the drive shaft, which is covered with a nonrotating catheter for most of its length, is advanced over a pre-inserted guide wire until the material removal instrument is positioned just proximal to the occluded site. The motor or turbine then rotates the drive shaft and the material removal instrument as the material removal instrument is moved transversely through the occluded portion of the vessel. The material removal instrument removes the material from the vessel rather than merely displacing or reforming the material as in a balloon angioplasty procedure.

Ablative atherectomy devices use a rotating ablation burr to remove occluding deposits in the patient's vasculature. The ablation burr is typically a small, ellipsoidal burr having an abrasive outer surface that is passed through the site of the occlusion while rotating at relatively high speeds, generally 50,000 to 200,000 rotations per minute. It has been found that healthy vascular tissue is pliable enough to resist ablation by the burr, but atherosclerotic plaques are less pliable and therefore are selectively removed by ablation.

With any atherectomy device, it is desirable to reduce the irritation and collateral damage to healthy vascular tissues during an ablation atherectomy procedure. In U.S. Pat. No. 6,015,420 to Wulfman et al., which is commonly owned by the assignee of the present application, an ablation burr is disclosed that has an abrasive coating only on a portion of the burr that is disposed radially inwardly from the burr maximum diameter, and therefore substantially prevents the abrasive portion of the burr from contacting the vessel walls. It has been found, however, that in some circumstances it can be difficult to move the burr transversely through heavily occluded vessels.

Given the above-discussed considerations, it is desirable to provide an atherectomy device having an ablation burr that can reduce irritation to the vessel walls while also facilitating moving the burr through the occluded region of the vessel.

SUMMARY OF THE INVENTION

The present invention overcomes many of the disadvantages of the prior art by providing an ablation burr for a rotational atherectomy device that reduces the risk of damage to a vessel wall while providing an ablative surface that has a diameter substantially equal to the maximum diameter of the ablation burr. The ablation burr according to the present invention utilizes two abrasive surfaces that are disposed on a leading portion of the burr body, a less aggressive abrasive surface is disposed on a portion of the burr nearest the vessel wall, and a more aggressive abrasive surface is disposed on a portion of the burr that is generally disposed further away from the vessel wall.

According to one embodiment of the present invention, the ablation burr has a smooth back surface and a leading surface wherein the leading surface has a first portion near the burr maximum diameter that is less abrasive and a second portion closer to the burr axis that is more abrasive.

In one aspect of the invention, the abrasive surfaces are composed of abrasive particles such as diamond affixed to the burr body. In another aspect of the invention, the abrasive surfaces are formed by etching, micromachining, or otherwise roughing the surface of the burr body.

In one embodiment of the present invention, the less abrasive first portion of the leading surface of the burr is generally convex and the more abrasive second portion of the leading surface is generally concave.

BRIEF DESCRIPTION OF THE DRAWINGS

The foregoing aspects and many other attendant advantages of the present invention will become more readily appreciated as the same become better understood by reference to the following detailed description, when taken in conjunction with the accompanying drawings, in which like reference numerals designate like parts throughout the figures and wherein.

DETAILED DESCRIPTION OF THE PREFERRED EMBODIMENT

Figure 1:
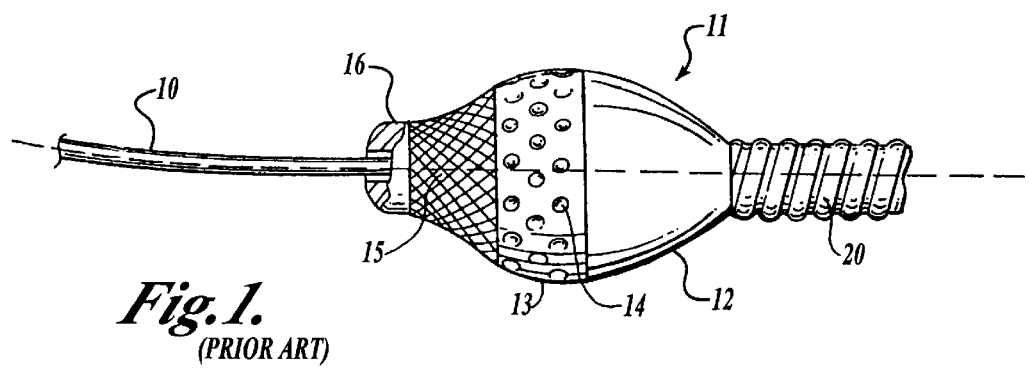
FIG. 1 is a side elevation view of a prior art rotational atherectomy ablation burr.

FIG. 1 is a side elevational view showing a prior art rotational atherectomy ablation burr 11. The ablation burr 11 is connected to a flexible drive shaft 20 and has a guide wire 10 running axially therethrough. The back or proximal portion 12 of the burr 11 is generally a half-ellipsoid with a smooth outer surface. The front or distal portion of the burr 11 includes a nonabrasive surface 13 that extends forwardly from the axial location of the burr's maximum diameter. The nonabrasive surface 13 is generally convex, decreasing in diameter from the burr's maximum diameter to a smaller diameter and has a number of dimples 14 formed therein to reduce the friction between the burr 11 and the vessel wall. The burr 11 also has an abrasive surface 15 disposed distally from the nonabrasive surface 13. The abrasive surface 15 is generally concave and decreases in diameter from the nonabrasive surface 13 to a cylindrical nose portion 16 at the distal tip of the burr 11. As can be seen most clearly in FIG. 1, the abrasive surface 15 of the burr 11 has a smaller maximum diameter than the maximum diameter of the burr 11. The burr 11 is designed to avoid contact between the abrasive surface 15 and the wall of the vessel into which it is inserted.

Figure 2:
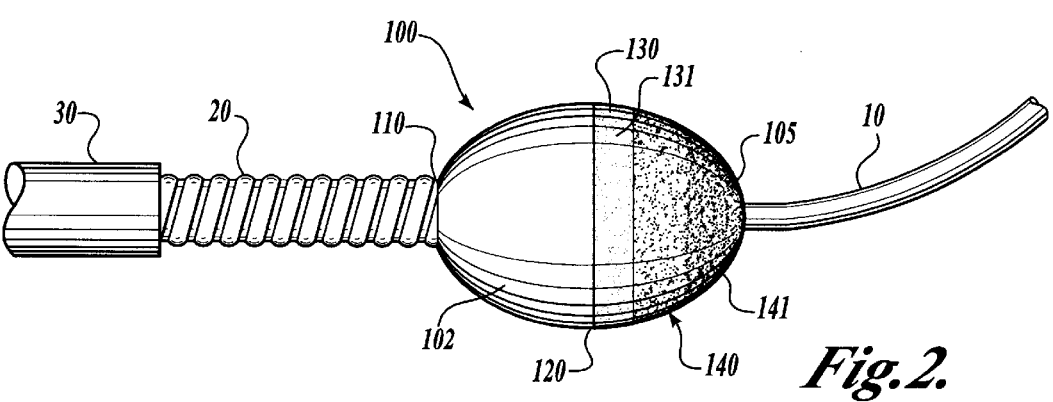
FIG. 2 is a side elevation view of a first embodiment of a rotational atherectomy ablation burr of the present invention.

A first embodiment of an atherectomy burr, according to the present invention, is shown in FIG. 2, which shows an elevation side view of an ablation burr 100 that is generally ellipsoid in shape. The burr 100 is connected at a proximal end 110 to a flexible drive shaft 20 which is covered for a substantial portion of its length by a nonrotating catheter 30. During use, guide wire 10 extends axially through the drive shaft 20 and the burr 100.

The burr 100 has a back surface 102 extending from a proximal end 110 of the burr to a point 120 at approximately the maximum diameter of the burr. A first leading surface 130 extends distally from the back surface 102. The first leading surface 130 is generally convex and decreases in diameter from the burr's maximum diameter at the point 120. In a preferred embodiment of the burr 100, the first leading surface 130 is coated with small abrasive particles 131, preferably having a characteristic linear dimension of less than about 20 microns, and more preferably less than about 10 microns. As used herein, the characteristic linear dimension refers to the diameter or some similar linear dimension used to characterize the size of the referenced abrasive particles. A second leading surface 140 that is generally convex in profile extends distally from the first leading surface 130. The second leading surface 140 decreases in diameter from the point where it meets the first leading surface to the distal end 105 of the burr 100. In a preferred embodiment, the second leading surface 140 is coated with larger abrasive particles 141, preferably having a characteristic linear dimension of between 10 and 50 microns, and more preferably between 20 and 30 microns. The small abrasive particles 131 and larger abrasive particles 141 comprise particles of diamond; however, other abrasive materials are also contemplated within the scope of this invention. It is also contemplated that the abrasive surfaces could be formed by etching, micromachining, or otherwise roughing the surface of a burr to produce an ablative topography.

Figure 3:
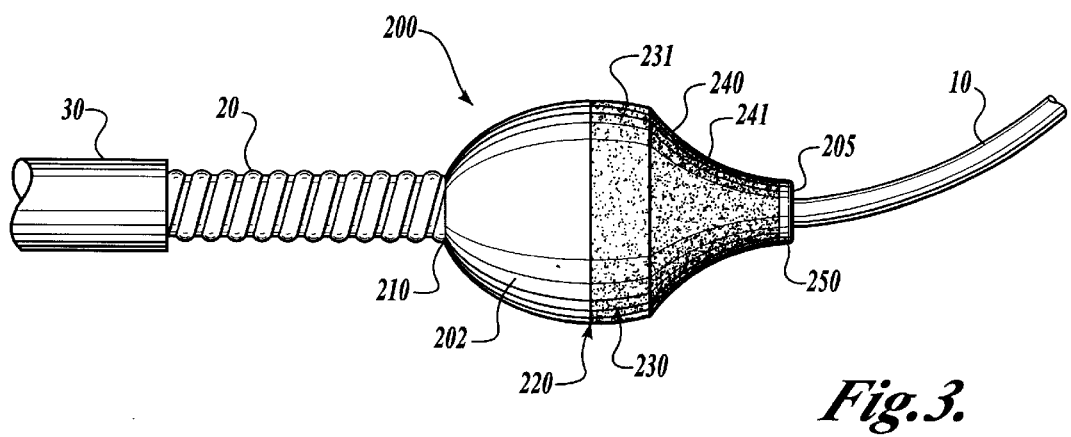
FIG. 3 is a side elevation view of a second embodiment of a rotational atherectomy ablation burr of the present invention.

A second embodiment according to the present invention is shown in FIG. 3, which is a side elevation view of an ablation burr 200 connected at a proximal end 210 to a drive shaft 20. The drive shaft 20 is again covered along a substantial portion of its length by a nonrotating catheter 30. The ablation burr 200 has a back surface 202 that is generally smooth and shaped approximately as a half ellipsoid. Extending distally from the back surface 202 at a point 220 of the burr's maximum diameter is a first leading surface 230 that is generally convex, and decreases in diameter from the burr's maximum diameter. In a preferred embodiment, the first leading surface 230 is coated with small abrasive particles 231, that preferably have a characteristic linear dimension less than about 20 microns, and more preferably less than about 10 microns. A second leading surface 240 extends distally from the first leading surface 230 to a minimum diameter at a narrow nose portion 250 having a smooth outer surface. The smooth nose portion 250 is intended to prevent any accidental damage to the guide wire 10. The second leading surface 240 is generally concave in profile having a diameter that increases slowly from the nose portion 250 and more rapidly near the point where the second leading surface adjoins the first leading surface 230. The second leading surface 240 is coated with larger abrasive particles 241 that have a characteristic linear dimension that preferably is about 10–50 microns, and more preferably about 20 to 30 microns.

Although this preferred embodiment is described with the convex portion having smaller abrasive particles and the concave portion having larger particles, it will be appreciated that this invention also comprehends variations in this configuration. For example, the smaller abrasive particles may extend into the concave portion of the burr, or alternatively, the larger abrasive particles may extend into the convex portion of the burr.

Figure 4:
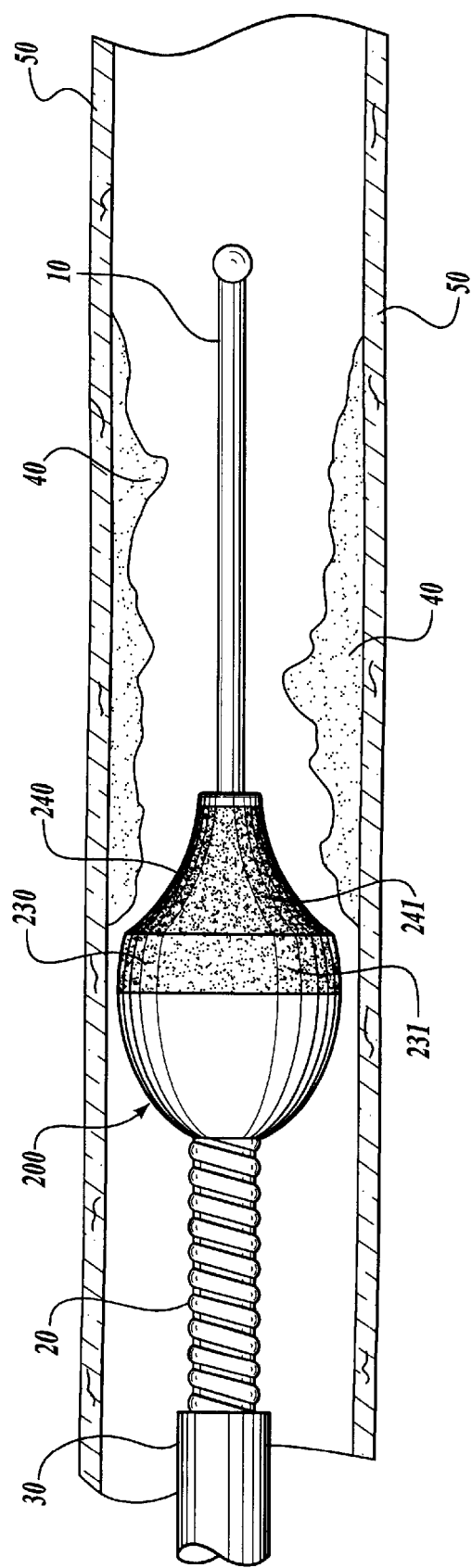
FIG. 4 is a side elevation view of the ablation burr shown in FIG. 3 showing the ablation burr in vivo at the site of an occlusion.

FIG. 4 shows the burr 200 disposed within the walls of a vessel 50 near the site of an occlusion 40. In operation, the burr 200 is rotationally driven by the flexible drive shaft 20 while being pushed laterally through the occlusion 40. It will be appreciated that the first abrasive surface 230 has a maximum diameter at least as great as the maximum diameter of the burr 200. The abrasive surfaces of the burr 230, 240 will therefore cut a channel through the occlusion 40 that is large enough to accommodate the burr 200. Only the less abrasive first leading surface 230 is disposed near the walls of the vessel 50, thereby minimizing irritation and/or damage to the walls of the vessel 50. The more abrasive second leading surface 240 provides a more aggressive ablative surface to more easily remove the occlusion 40. It will also be appreciated that the first leading surface 230 is disposed near the vessel wall 50 at a relatively shallow angle, and therefore will ablate only a very narrow portion of the occlusion 40 nearest the vessel wall. The bulk of the occlusion 40 will be removed by the second leading surface 240.

Figure 5:
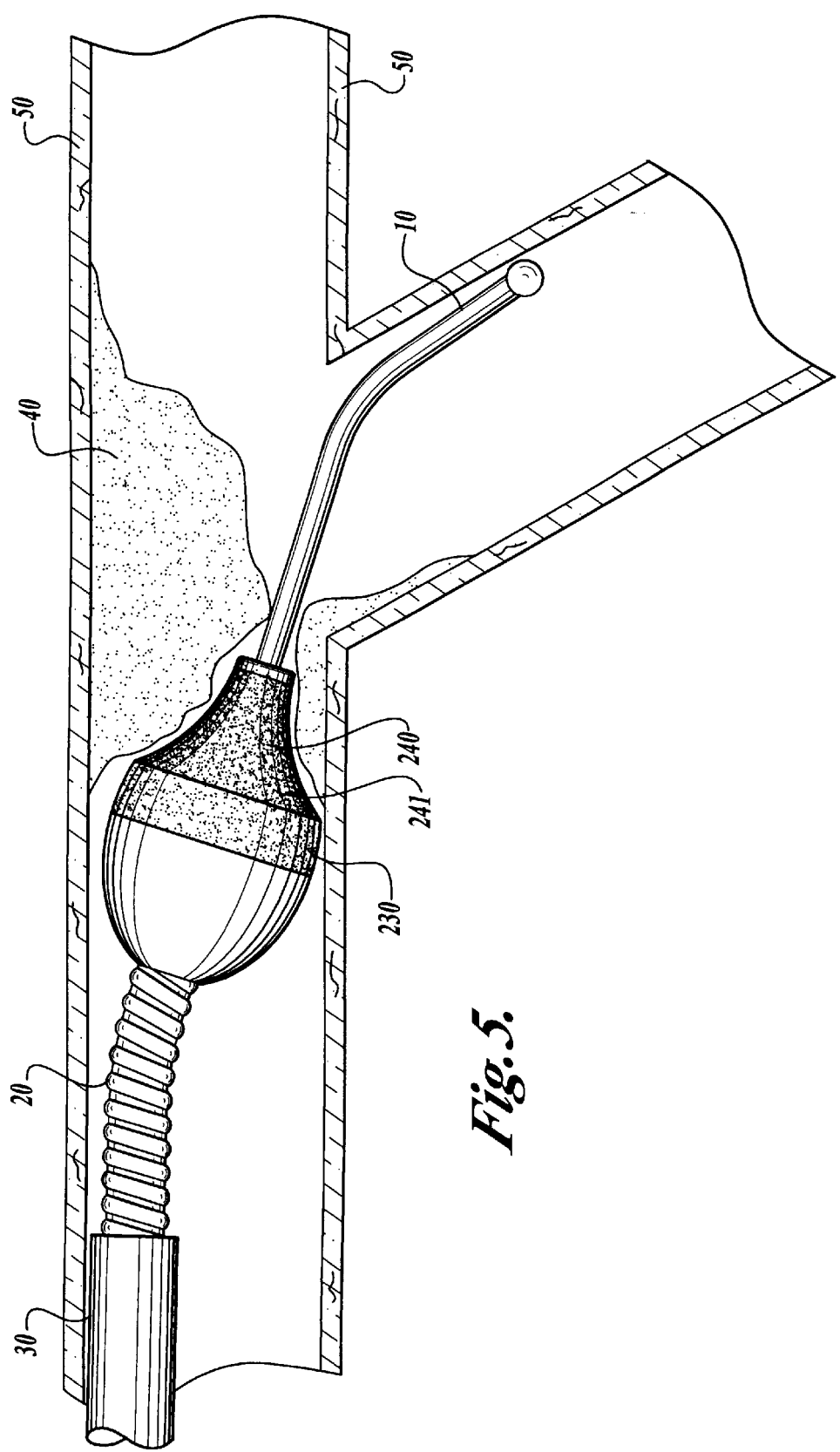
FIG. 5 is a side elevation view of the ablation burr shown in FIG. 3 showing the ablation burr in vivo at the site of an asymmetric occlusion and/or tortuous vascular path, wherein the ablation burr has rotated with respect to the axis of a vessel.

When the burr 200 encounters tortuous vascular paths and/or occlusions 40 that are not symmetrically disposed within the vessel 50, as shown in FIG. 5, the ablation burr 200 will not always be axially aligned with the vessel. As can be seen in FIG. 5, because the second leading surface 240 is concave, even if the ablation burr 200 is tilted significantly from the vessel axis, contact between the larger abrasive particles 241 and the vessel wall 50 is limited. In fact the tilting of the ablation burr 200 may beneficially cause a greater proportion of the larger abrasive particles 241 to contact the occlusion 40.

Figure 6:
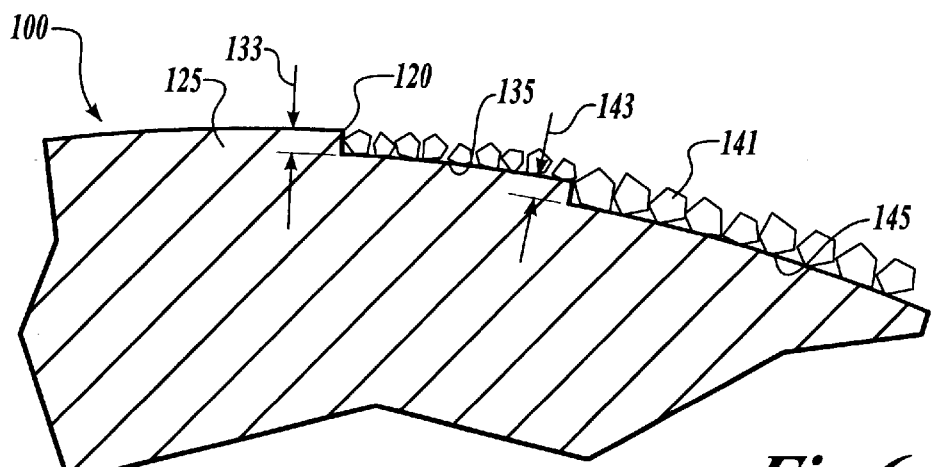
FIG. 6 is a partial cutaway cross-sectional view of the ablation burr shown in FIG. 3 showing the burr body near the location of the burr maximum diameter.

FIG. 6 shows an enlarged cross-sectional view of a portion of the ablation burr 100 shown in FIG. 2 near the point of maximum diameter 120. In this embodiment, a burr blank, or body 125, onto which the abrasive particles 131 and 141 are deposited, has an inwardly stepped or offset portion 135 that underlies the small abrasive particles 131 on the first leading surface 130. The depth of the offset 133 is selected to be approximately equal to the characteristic linear dimension of the small abrasive particles 131. The burr body 125 also has a second offset or stepped surface 145 that underlies the larger abrasive particles 141 on the second leading surface 140. The depth of the offset 143 is selected to be approximately equal to the difference between the characteristic linear dimension of the larger abrasive particles 141 and the characteristic linear dimension of the small abrasive particles 131. It will be appreciated that the burr body 125 and the abrasive particles 131 and 141 will therefore provide a relatively smooth profile to the occlusion 40. Moreover, when the burr 100 is removed from the patient's vasculature, the abrasive surface will not project radially out from the smooth back surface 102 (or the extent of any such projection will be reduced), thereby reducing the risk of irritating other portions of the vessel walls. It will also be appreciated that in the second embodiment of the present invention, the burr 200 could also be provided with offset portions similar to those described above. In some instances it may be preferred to have the depth of the offset 133 less than the characteristic linear dimension of the small abrasive particles 131 so that the first leading surface 130 extends out slightly farther than the maximum diameter of the burr body 125.

Figure 7:
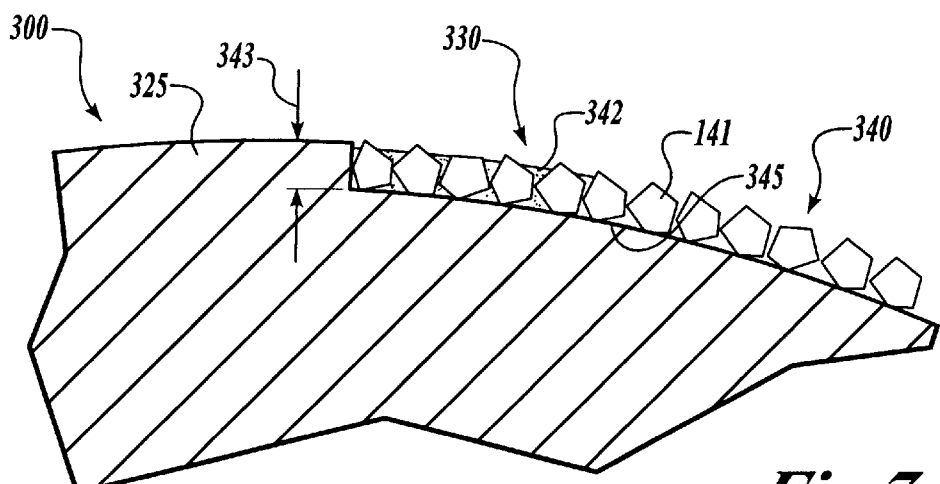
FIG. 7 is a partial cutaway cross-sectional view of another embodiment of an ablation burr of the present invention wherein a portion of the abrasive particles have been overplated as an alternative method of creating a less abrasive ablative surface.

FIG. 7 shows an enlarged cross-sectional view of a portion of the same region of a burr as shown in FIG. 6. In this alternative design, a burr 300 is shown with a burr blank 325 having a single offset or stepped portion 345. The offset portion 345 has a depth 343 that is selected to be approximately equal to the characteristic linear dimension of the larger abrasive particles 141. In this embodiment of the burr, both a first leading surface 330 and a second leading surface 340 are coated with larger abrasive particles 141. After the larger abrasive particles 141 are affixed to the burr blank 325, the first abrasive surface 330 is provided with an overplating or overcoating of a material 342 such as nickel. The nickel layer builds up between the larger abrasive particles 141 on the first leading surface 330, reducing the effective height of these larger abrasive particles 141 and thereby forming a less abrasive surface.

Figure 8:
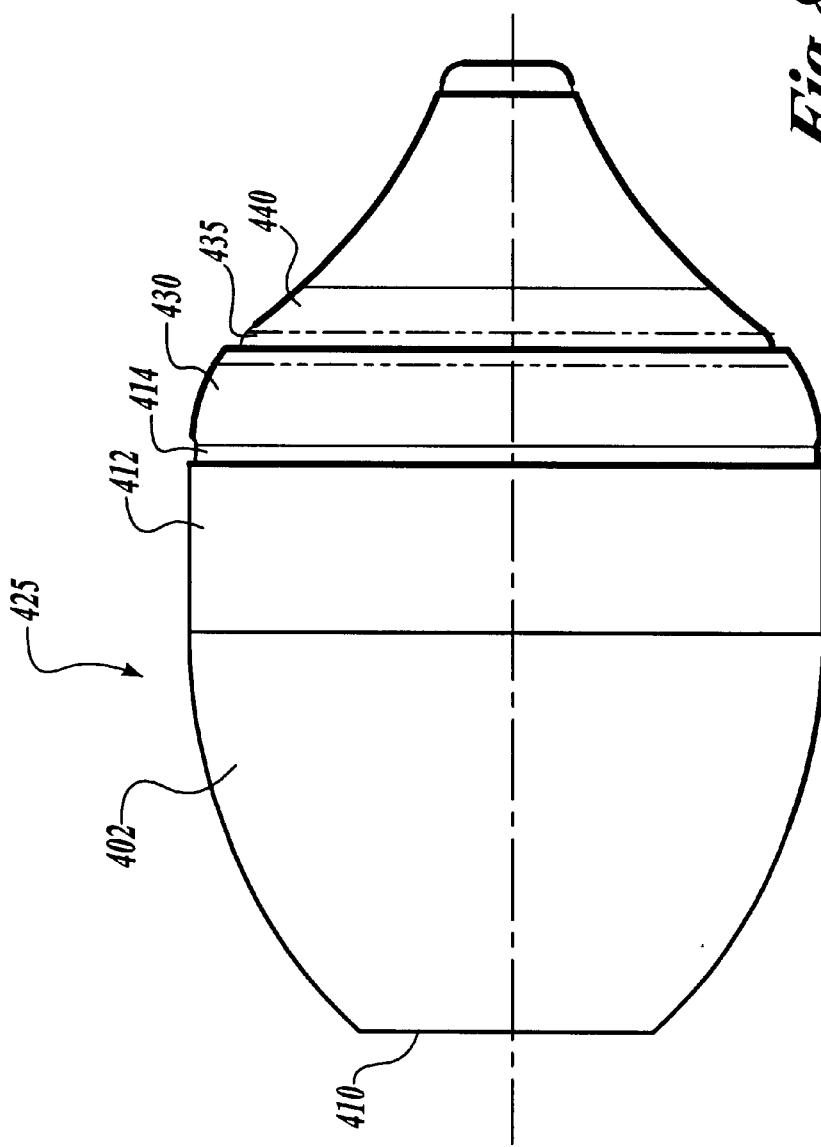
FIG. 8 is a side view of a burr blank for another embodiment of an ablation burr of the present invention.

Another preferred embodiment of a burr body or blank according to the present invention is shown in FIG. 8, wherein a burr blank or body 425 is depicted. The burr body 425 includes a smooth back surface 402 that is generally convex. The proximal end 410 of the burr body 425 is adapted to receive a flexible drive shaft (not shown). A constant diameter portion 412 extends from the distal end of the back surface 402, terminating with an inwardly offset scribe line 414. The constant diameter portion 412 and scribe line 414 have been found useful in the manufacturing process, providing a graspable area and a more visible demarcation indicator, respectively.

A generally convex first leading surface 430 extends distally from the scroll line 414. A generally concave second leading surface 440 extends distally from the first leading surface 430, and is inwardly offset from the first leading surface 430 at the location that the first and second leading surfaces adjoin. As shown in FIG. 8, the second leading surface 440 includes a proximal portion 435 that is convex, before inflecting to a generally concave geometry. In a preferred embodiment, the larger abrasive particles 141 are first affixed to the second leading surface 440 (including the convex portion 435), and then the smaller abrasive particles 131 are affixed to the first leading portion 430, the small abrasive particles 131 being allowed to overlap the larger abrasive particles 141 generally at the second leading surface convex portion 435. This manufacturing method has been found to produce a relatively smooth burr profile.

Although the preferred embodiments have been described with two abrasive zones, it will be readily apparent to one of ordinary skill in the art that more than one abrasive zone could also be used. While the preferred embodiment of the invention has been illustrated and described, it will be appreciated that various changes can be made therein without departing from the scope of the invention. It is therefore intended that the scope of the invention be determined solely from the following claims and equivalents thereto.

The embodiments of the invention in which an exclusive property or privilege is claimed are defined as follows:

1. An ablation burr for removing deposits from a patient's vessel, the ablation burr comprising:
   a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;
   a plurality of first abrasive particles having a first characteristic linear dimension that are affixed to the first surface;
   a plurality of second abrasive particles having a second characteristic linear dimension that is less than the first characteristic linear dimension, the second abrasive particles being affixed to the second surface; and wherein the first abrasive particles comprise diamond particles.

2. An ablation burr for removing deposits from a patient's vessel, the ablation burr comprising:

a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein the first characteristic linear dimension is less than about 20 microns.

3. An ablation burr for removing deposits from a patient's vessel, the ablation burr comprising:

a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein the first characteristic linear dimension is less than about 10 microns.

4. An ablation burr for removing deposits from a patient's vessel, the ablation burr comprising:

a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein the second abrasive particles comprise diamond particles.

5. An ablation burr for removing deposits from a patient's vessel, the ablation burr comprising:

a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein the second characteristic linear dimension is between about 10 and 50 microns.

6. An ablation burr for removing deposits from a patient's vessel, the ablation burr comprising:

a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein the second characteristic linear dimension is between about 20 and 30 microns.

7. An ablation burr for removing deposits from a patient's vessel, the ablation burr comprising:

a burr body having a proximal end, a distal end and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein the first surface is convex along a substantial portion of its length.

8. The ablation burr according to claim 7, wherein the second surface is concave along a substantial portion of its length.

9. An ablation burr for removing deposits from a patient's vessel, the ablation burr comprising:

a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein the first surface has a trailing edge that is adjacent the back portion and the trailing edge is inwardly offset from the back portion by an amount approximately equal to the second characteristic linear dimension.

10. An ablation burr for removing deposits from a patient's vessel, the ablation burr comprising:

a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein the first surface has a trailing edge that is adjacent the back portion and the trailing edge is inwardly offset from the back portion by an amount approximately equal to the first characteristic linear dimension.

11. An ablation burr for removing deposits from a patient's vessel, the ablation burr comprising:

a burr body having a proximal end, a distal end, and a maximum diameter at an axial location between the proximal end and the distal end, wherein the burr body further comprises a back portion, a first surface disposed between the back portion and the distal end, and a second surface disposed between the first surface and the distal end of the burr;

a plurality of first abrasive particles having a first characteristic linear dimension that are affixed to the first surface;

a plurality of second abrasive particles having a second characteristic linear dimension that is less than the first characteristic linear dimension, the second abrasive particles being affixed to the second surface; and wherein:
  a. the first surface is convex;
  b. the second surface is concave;
  c. the first and second abrasive particles comprise diamond particles;
  d. the first characteristic linear dimension is less than about 20 microns; and
  e. the second characteristic linear dimension is between about 20 and 30 microns.

12. An ablation burr for removing deposits from a patient's vessel, comprising:

(a) a burr body having a proximal end and a distal end, the burr body comprising a back surface that increases in diameter from the proximal end to a burr maximum diameter, and a leading surface extending distally from the burr maximum diameter to the distal end;

(b) an abrasive leading surface, the abrasive leading surface having a characteristic abrasive dimension; and (c) an interstitial coating over a portion of the abrasive leading surface, the coating having a thickness that is less than the characteristic abrasive dimension whereby a portion of the abrasive leading surface projects out from the coating; and wherein the coating extends distally a distance from the burr maximum diameter.

13. An ablation burr for removing deposits from a patient's vessel, comprising:

(a) a burr body having a proximal end and a distal end, the burr body comprising a back surface that increases in diameter from the proximal end to a burr maximum diameter, and a leading surface extending distally from the burr maximum diameter to the distal end;

(b) an abrasive leading surface, the abrasive leading surface having a characteristic abrasive dimension; and (c) an interstitial coating over a portion of the abrasive leading surface, the coating having a thickness that is less than the characteristic abrasive dimension whereby a portion of the abrasive leading surface projects out from the coating; and wherein the abrasive leading surface comprises diamond particles affixed to a nonabrasive burr body.

14. The ablation burr of claim 13, wherein the interstitial coating comprises nickel.

15. An atherectomy device for removing deposits from a vessel wall, comprising:

(a) a flexible drive shaft; and (b) an ablation burr comprising a back portion that is coupled to the flexible drive shaft, and a front portion having a continuously decreasing diameter that extends distally from the back portion, the front portion having a first outer surface coated with a first abrasive and a second outer surface that extends distally from the first outer surface and is coated with a second abrasive, wherein the first abrasive is finer than the second abrasive; and wherein the first abrasive comprises diamond particles.

16. An atherectomy device for removing deposits from a vessel wall, comprising:

(a) a flexible drive shaft; and (b) an ablation burr comprising a back portion that is coupled to the flexible drive shaft, and a front portion having a continuously decreasing diameter that extends distally from the back portion, the front portion having a first outer surface coated with a first abrasive and a second outer surface that extends distally from the first outer surface and is coated with a second abrasive, wherein the first abrasive is finer than the second abrasive; and wherein the second abrasive comprises diamond particles.

17. An atherectomy device for removing deposits from a vessel wall, comprising:

(a) a flexible drive shaft; and (b) an ablation burr comprising a back portion that is coupled to the flexible drive shaft, and a front portion having a continuously decreasing diameter that extends distally from the back portion, the front portion having a first outer surface coated with a first abrasive and a second outer surface that extends distally from the first outer surface and is coated with a second abrasive, wherein the first abrasive is finer than the second abrasive; and wherein the first outer surface is convex and the second outer surface is concave.

18. An atherectomy device for removing deposits from a vessel wall, comprising:

(a) a flexible drive shaft; and (b) an ablation burr comprising a back portion that is coupled to the flexible drive shaft, and a front portion having a continuously decreasing diameter that extends distally from the back portion, the front portion having a first outer surface coated with a first abrasive and a second outer surface that extends distally from the first outer surface and is coated with a second abrasive, wherein the first abrasive is finer than the second abrasive; and wherein the first abrasive has a maximum linear dimension less than about 20 microns and the second abrasive has a maximum linear dimension between about 20 and 50 microns.

19. An atherectomy device for removing deposits from a vessel wall, comprising:

(a) a flexible drive shaft; and (b) an ablation burr comprising a back portion that is coupled to the flexible drive shaft, and a front portion having a continuously decreasing diameter that extends distally from the back portion, the front portion having a first outer surface coated with a first abrasive and a second outer surface that extends distally from the first outer surface and is coated with a second abrasive, wherein the first abrasive is finer than the second abrasive; and wherein the first abrasive has a maximum linear dimension less than approximately 10 microns and the second abrasive has a maximum linear dimension between about 20 and 30 microns.

20. An atherectomy device for removing deposits from a vessel wall, comprising:

(a) a flexible drive shaft; and (b) an ablation burr comprising a back portion that is coupled to the flexible drive shaft, and a front portion having a continuously decreasing diameter that extends distally from the back portion, the front portion having a first outer surface coated with a first abrasive and a second outer surface that extends distally from the first outer surface and is coated with a second abrasive, wherein the first abrasive is finer than the second abrasive; and wherein the ablation burr further comprises a nose portion that extends distally from the front portion, the nose portion having a smooth outer surface.

21. An ablation burr for removing deposits from a patient's vessel, comprising:

(a) a rearward portion having a proximal end and a distal end, the proximal end being adapted to receive an end of a drive shaft; and (b) a forward portion extending distally from the distal end of the rearward portion, the forward portion comprising a first section disposed adjacent to the rearward portion and a second section disposed distally from the first section wherein the first section has a first outer abrasive surface and the second section has a second outer abrasive surface that is less abrasive than the first outer abrasive surface;

wherein the burr is formed from a unitary burr blank.

22. The ablation burr of claim 21, wherein the first and second abrasive surfaces are formed by roughing the surface of a portion of the burr blank.

23. The ablation burr of claim 21 wherein the first and second abrasive surfaces are formed by etching away a portion of the burr blank.

* * * * *